(12) United States Patent
Cholli et al.

(10) Patent No.: US 7,767,853 B2
(45) Date of Patent: Aug. 3, 2010

(54) ANTIOXIDANTS AND METHODS OF MAKING AND USING THE SAME

(75) Inventors: Ashok L. Cholli, Chelmsford, MA (US); Rajesh Kumar, Groton, CT (US); Taizoon Canteenwala, Lowell, MA (US); Vijayendra Kumar, Dracut, MA (US)

(73) Assignee: Polnox Corporation, Lowell, MA (US)

( * ) Notice: Subject to any disclaimer, the term of this patent is extended or adjusted under 35 U.S.C. 154(b) by 378 days.

(21) Appl. No.: 11/975,141

(22) Filed: Oct. 17, 2007

(65) Prior Publication Data

US 2008/0249335 A1 Oct. 9, 2008

Related U.S. Application Data

(60) Provisional application No. 60/853,275, filed on Oct. 20, 2006.

(51) Int. Cl.
C07C 233/05 (2006.01)
C09K 15/16 (2006.01)

(52) U.S. Cl. .................. 564/158; 252/399; 252/401; 252/407; 426/601

(58) Field of Classification Search ............... 564/158; 252/399, 401, 407; 426/601
See application file for complete search history.

(56) References Cited

U.S. PATENT DOCUMENTS

| | | | |
|---|---|---|---|
| 3,294,836 A | 12/1966 | Peterson et al. |
| 3,441,545 A | 4/1969 | Blatz, et al. |
| 3,459,704 A | 8/1969 | Peterson, et al. |
| 3,557,245 A | 1/1971 | Phillips et al. |
| 3,632,785 A | 1/1972 | Bornstein |
| 3,645,970 A | 2/1972 | Kleiner |
| 3,649,667 A | 3/1972 | Song et al. |
| 3,655,831 A | 4/1972 | Friedman |
| 3,870,680 A | 3/1975 | Schurdak |
| 3,907,939 A | 9/1975 | Robin, et al. |
| 3,953,402 A | 4/1976 | Kline |
| 3,965,039 A | 6/1976 | Chaplits et al. |
| 3,983,091 A | 9/1976 | Gloth et al. |
| 3,996,160 A | 12/1976 | Dale et al. |
| 3,996,198 A | 12/1976 | Wang et al. |
| 4,054,676 A | 10/1977 | Weinshenker et al. |
| 4,094,857 A | 6/1978 | Wolfe, Jr. |
| 4,096,319 A | 6/1978 | Willette et al. |
| 4,097,464 A | 6/1978 | Kline |
| 4,098,829 A | 7/1978 | Weinshenker et al. |
| 4,107,144 A | 8/1978 | Russell et al. |
| 4,136,055 A | 1/1979 | Lyons |
| 4,202,816 A | 5/1980 | Moser et al. |
| 4,205,151 A | 5/1980 | Dale et al. |
| 4,213,892 A | 7/1980 | Scott |
| 4,219,453 A | 8/1980 | Sakurai et al. |
| 4,267,358 A | 5/1981 | Hechenbleikner et al. |
| 4,281,192 A | 7/1981 | Jacquet et al. |
| 4,283,572 A | 8/1981 | Klicker |
| 4,317,933 A | 3/1982 | Parker |
| 4,341,879 A | 7/1982 | Sugio et al. |
| 4,355,148 A | 10/1982 | Layer et al. |
| 4,377,666 A | 3/1983 | Farrar |
| 4,380,554 A | 4/1983 | Serres, Jr. |
| 4,447,657 A | 5/1984 | Firth et al. |
| 4,465,871 A | 8/1984 | Firth et al. |
| 4,510,296 A | 4/1985 | Hergenrother |
| 4,511,491 A | 4/1985 | Ishii et al. |
| 4,690,995 A | 9/1987 | Keskey et al. |
| 4,761,247 A | 8/1988 | Rei et al. |
| 4,824,929 A | 4/1989 | Arimatsu et al. |
| 4,849,503 A | 7/1989 | Cotter et al. |
| 4,855,345 A | 8/1989 | Rosenberger et al. |
| 4,857,596 A | 8/1989 | MacLeay et al. |
| 4,870,214 A | 9/1989 | Mina et al. |
| 4,894,263 A | 1/1990 | Dubois et al. |
| 4,897,438 A | 1/1990 | Kikuchi et al. |
| 4,900,671 A | 2/1990 | Pokora et al. |
| 4,925,591 A | 5/1990 | Nakauchi et al. |
| 4,968,759 A | 11/1990 | Kikuchi et al. |
| 4,977,004 A | 12/1990 | Bettle, III et al. |
| 4,981,917 A | 1/1991 | MacLeay et al. |
| 4,994,628 A | 2/1991 | Goddard et al. |
| 5,013,470 A | 5/1991 | Benfaremo |

(Continued)

FOREIGN PATENT DOCUMENTS

CS 111291 6/1964

(Continued)

OTHER PUBLICATIONS

RN 85650-63-1, 1984.*

(Continued)

*Primary Examiner*—Shailendra Kumar
(74) *Attorney, Agent, or Firm*—Hamilton, Brook, Smith & Reynolds, P.C.

(57) ABSTRACT

The present invention is directed to a compound represented by Structural Formula I:

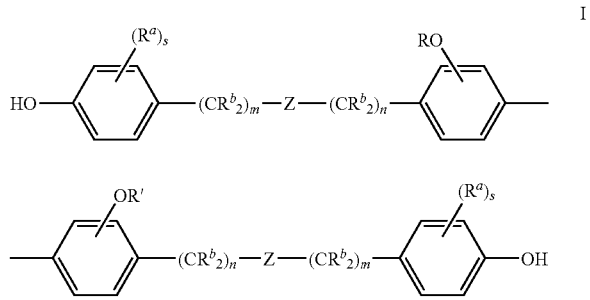

wherein the variables are described herein. Also included are methods of making the compounds of Structural Formula (I) and methods of using the compounds as antioxidants.

33 Claims, 1 Drawing Sheet

U.S. PATENT DOCUMENTS

| | | |
|---|---|---|
| 5,017,727 A | 5/1991 | Olivier |
| 5,082,358 A | 1/1992 | Tabata et al. |
| 5,102,962 A | 4/1992 | Kikuchi et al. |
| 5,117,063 A | 5/1992 | Stern et al. |
| 5,143,828 A | 9/1992 | Akkara et al. |
| 5,185,391 A | 2/1993 | Stokich, Jr. |
| 5,185,407 A | 2/1993 | Wong |
| 5,188,953 A | 2/1993 | Johnson et al. |
| 5,191,008 A | 3/1993 | Frost et al. |
| 5,196,142 A | 3/1993 | Mollet et al. |
| 5,206,303 A | 4/1993 | Tse et al. |
| 5,207,939 A | 5/1993 | Farng et al. |
| 5,274,060 A | 12/1993 | Schadeli |
| 5,278,055 A | 1/1994 | Cyrus, Jr. et al. |
| 5,304,589 A | 4/1994 | Davidson et al. |
| 5,320,889 A | 6/1994 | Bettle, III |
| 5,449,715 A | 9/1995 | Plochocka et al. |
| 5,498,809 A | 3/1996 | Emert et al. |
| RE35,247 E | 5/1996 | Cyrus, Jr. et al. |
| 5,516,856 A | 5/1996 | Sanchez |
| 5,541,091 A | 7/1996 | Wheeler et al. |
| 5,565,300 A | 10/1996 | Uenishi et al. |
| 5,574,118 A | 11/1996 | Olivier |
| 5,652,201 A | 7/1997 | Papay et al. |
| 5,739,341 A | 4/1998 | Dubs et al. |
| 5,834,544 A | 11/1998 | Lin et al. |
| 5,837,798 A | 11/1998 | Hutchings et al. |
| 5,869,592 A | 2/1999 | Gagne et al. |
| 5,911,937 A | 6/1999 | Hekal |
| 5,994,498 A | 11/1999 | Tripathy et al. |
| 6,018,018 A | 1/2000 | Samuelson et al. |
| 6,046,263 A | 4/2000 | Rasberger et al. |
| 6,096,695 A | 8/2000 | Lam et al. |
| 6,096,859 A | 8/2000 | Akkara et al. |
| 6,150,491 A | 11/2000 | Akkara |
| 6,232,314 B1 | 5/2001 | Jarrott et al. |
| 6,342,549 B1 | 1/2002 | Hirose et al. |
| 6,444,450 B2 | 9/2002 | Akkara et al. |
| 6,646,035 B2 | 11/2003 | Koch et al. |
| 6,723,815 B2 | 4/2004 | Callaghan et al. |
| 6,743,525 B2 | 6/2004 | Bernsten et al. |
| 6,770,785 B1 | 8/2004 | Desai et al. |
| 6,794,480 B2 | 9/2004 | Goto et al. |
| 6,800,228 B1 | 10/2004 | Semen |
| 6,828,364 B2 | 12/2004 | Gugumus |
| 7,132,496 B2 | 11/2006 | Kerres et al. |
| 7,169,844 B2 | 1/2007 | Inokami |
| 7,205,350 B2 | 4/2007 | Thibaut |
| 7,223,432 B2 | 5/2007 | Cholli et al. |
| 7,262,319 B2 | 8/2007 | Rehm et al. |
| 2001/0041203 A1 | 11/2001 | Uno et al. |
| 2002/0007020 A1 | 1/2002 | Higashimura et al. |
| 2002/0128493 A1 | 9/2002 | Romanczyk, Jr. et al. |
| 2002/0143025 A1 | 10/2002 | Pratt et al. |
| 2002/0183470 A1 | 12/2002 | Tripathy et al. |
| 2003/0030033 A1 | 2/2003 | Duyck et al. |
| 2003/0078346 A1 | 4/2003 | Nakamura et al. |
| 2003/0091837 A1 | 5/2003 | Aoki |
| 2003/0176620 A1 | 9/2003 | Romanczyk, Jr. et al. |
| 2003/0191242 A1 | 10/2003 | Zedda et al. |
| 2003/0229196 A1 | 12/2003 | Braat et al. |
| 2003/0230743 A1 | 12/2003 | Cholli et al. |
| 2004/0015021 A1 | 1/2004 | Adams et al. |
| 2004/0164279 A1 | 8/2004 | Stevenson et al. |
| 2004/0180994 A1 | 9/2004 | Pearson et al. |
| 2004/0186167 A1 | 9/2004 | Dou et al. |
| 2004/0186214 A1 | 9/2004 | Li et al. |
| 2004/0198875 A1 | 10/2004 | Kaprinidis et al. |
| 2004/0214935 A1 | 10/2004 | Cholli et al. |
| 2005/0170978 A1 | 8/2005 | Migdal et al. |
| 2005/0209379 A1 | 9/2005 | Botkin et al. |
| 2005/0238789 A1 | 10/2005 | Cholli et al. |
| 2005/0242328 A1 | 11/2005 | Baranski |
| 2006/0029706 A1 | 2/2006 | Cholli et al. |
| 2006/0040833 A1 | 2/2006 | Al-Akhdar et al. |
| 2006/0041087 A1 | 2/2006 | Cholli |
| 2006/0041094 A1 | 2/2006 | Cholli |
| 2006/0128929 A1 | 6/2006 | Yang et al. |
| 2006/0128930 A1 | 6/2006 | Dhawan et al. |
| 2006/0128931 A1 | 6/2006 | Kumar et al. |
| 2006/0128939 A1 | 6/2006 | Kumar et al. |
| 2006/0154818 A1 | 7/2006 | Destro et al. |
| 2006/0189820 A1 | 8/2006 | Rehm et al. |
| 2006/0189824 A1 | 8/2006 | Kumar et al. |
| 2006/0208227 A1 | 9/2006 | Shiraki |
| 2006/0233741 A1 | 10/2006 | Kumar et al. |
| 2007/0010632 A1 | 1/2007 | Kaplan et al. |
| 2007/0106059 A1 | 5/2007 | Cholli et al. |
| 2007/0135539 A1 | 6/2007 | Cholli et al. |
| 2007/0149660 A1 | 6/2007 | Kumar et al. |
| 2007/0154430 A1 | 7/2007 | Cholli et al. |
| 2007/0154608 A1 | 7/2007 | Cholli et al. |
| 2007/0154720 A1 | 7/2007 | Cholli et al. |
| 2007/0161522 A1 | 7/2007 | Cholli et al. |
| 2008/0249335 A1 | 10/2008 | Cholli et al. |
| 2008/0293856 A1 | 11/2008 | Kumar et al. |
| 2008/0311065 A1 | 12/2008 | Cholli |
| 2009/0184294 A1 | 7/2009 | Cholli et al. |

FOREIGN PATENT DOCUMENTS

| | | |
|---|---|---|
| DE | 197 47 644 A1 | 5/1999 |
| DE | 198 43 875 A1 | 3/2000 |
| EP | 0 181 023 A1 | 5/1986 |
| EP | 0 289 077 A2 | 11/1988 |
| EP | 0 358 157 | 3/1990 |
| EP | 0 404 039 A1 | 12/1990 |
| EP | 0 618 203 A1 | 10/1994 |
| EP | 0 688 805 A1 | 12/1995 |
| EP | 1 067 144 A1 | 1/2001 |
| EP | 1 468 968 A1 | 10/2004 |
| FR | 2 183 973 | 12/1973 |
| GB | 1 283 103 | 7/1972 |
| GB | 1 320 169 | 6/1973 |
| GB | 1 372 042 | 10/1974 |
| GB | 1 389 442 | 4/1975 |
| GB | 1 469 245 | 4/1977 |
| GB | 1 482 649 | 8/1977 |
| JP | 69002715 B | 1/1966 |
| JP | 43016392 B4 | 7/1968 |
| JP | 44024274 | 10/1969 |
| JP | 44028850 | 11/1969 |
| JP | 45 2980 | 1/1970 |
| JP | 49 29339 | 3/1974 |
| JP | 57085366 A | 5/1982 |
| JP | 59025814 | 2/1984 |
| JP | 59197447 | 11/1984 |
| JP | 60-199832 | 10/1985 |
| JP | 05 199858 | 8/1993 |
| JP | 06135876 A | 5/1994 |
| JP | 06 247959 | 9/1994 |
| JP | 08027226 A | 1/1996 |
| JP | 09262069 | 10/1997 |
| JP | 09 328519 | 12/1997 |
| JP | 09 328521 | 12/1997 |
| JP | 9322784 A | 12/1997 |
| JP | 11-80063 | 3/1999 |
| JP | 11-158103 | 6/1999 |
| JP | 2003138258 | 5/2003 |
| NL | 7 905 000 | 3/1980 |
| WO | WO 92/20734 | 11/1992 |
| WO | WO 00/39064 | 7/2000 |
| WO | WO 01/18125 A1 | 3/2001 |
| WO | WO 01/48057 A1 | 7/2001 |

| | | |
|---|---|---|
| WO | WO 02/079130 A1 | 10/2002 |
| WO | WO 03/087260 A1 | 10/2003 |
| WO | WO 03/102004 A1 | 12/2003 |
| WO | WO 2004/024070 A2 | 3/2004 |
| WO | WO 2004/050795 A2 | 6/2004 |
| WO | WO 2005/025513 A2 | 3/2005 |
| WO | WO 2005/025646 A2 | 3/2005 |
| WO | WO 2005/060500 A2 | 7/2005 |
| WO | WO 2005/070974 A2 | 8/2005 |
| WO | WO 2005/071005 A1 | 8/2005 |
| WO | WO 2006/018403 A1 | 2/2006 |
| WO | WO 2006/060801 A2 | 6/2006 |
| WO | WO 2006/104957 A2 | 10/2006 |
| WO | WO 2008/005358 A2 | 1/2008 |

OTHER PUBLICATIONS

Akkara, J.A., et al., "Hematin-Catalyzed Polymerization of Phenol Compounds," Macromolecules, 33(7):2377-2382 (2000).

Akkara, J.A., et al., "Synthesis and Characterization of Polymers Produced by Horseradish Peroxidase in Dioxane," J. of Polymer Science: Part A: Polymer Chemistry, 29(11):1561-1574 (1991).

Armengol, E., et al., "Acid Zeolites as Catalysts in Organic Reactions, tert-Butylation of Anthracene, Naphthalene and Thianthrene," Appl. Catal. A 149:411-423 (1997).

Ayyagari, M.S., et al., "Controlled Free-Radical Polymerization of Phenol Derivatives by Enzyme-Catalyzed Reactions in Organic Solvents," Macromolecules, 28(15):5192-5197 (1995).

Badamali, S.K., et al., "Influence of Aluminium Sources on the Synthesis and Catalytic Activity of Mesoporous AlMCM-41 Molecular Sieves," Catal. Today 63:291-295 (2000).

Belyaev, A., et al., "Structure-Activity Relationship of Diaryl Phosphonate Esters as Potent Irreversible Dipeptidyl Peptidase IV Inhibitors," J. Med. Chem., 42(6):1041-1052 (1998).

Blokhin, Y.I, et al., "Phosphorylation of Dihydric Phenols with Amides of Phosphorous Acid," Russian Chem. Bulletin, 45(9):2250-2251 (1996).

Bruno, F.F., et al., "Enzymatic Template Synthesis of Polyphenol," Materials Research Society Symposium Proceedings vol. 600, Electroactive Polymers (EAP):255-259 (1999).

Chandra, K.G. and Sharma, M.M., "Alkylation of Phenol with MTBE and Other tert-butylethers:Cation Exchange Resins as Catalysts," Catal. Lett. 19(4):309-317 (1993).

Circ-Marjanovic, et al., Chemical Oxidative Polymerization of Aminodiphenylamines, Journal of Physical Chemistry B, 112, 23: 6976-6987 (2008).

Coppinger, G.B., et al., "Photo-Fries Rearrangement of Aromatic Esters. Role of Steric and Electronic Factors" J. of Phy. Chem., 70(11):3479-3489 (1966).

Database CA [online] Chemical Abstracts Service, Columbus, Ohio, US, XP-002429584, Database Accession No. 81::153647, Organic Phosphate Stabilizers for Polyamides and Polyurethanes, abstract, Minagawa, M. (1974).

Database Caplus [online] Chemical Abstracts Service, Columbus, Ohio, US, XP-002387095, Database Accession No. 1981:572206, Effectiveness of Inhibitors in the Oxidation of Jet Fuel with an Initiator, abstract, Kovalev, et al.

Devassy, B.M., et al., "Zirconia Supported Phosphotungstic Acid as an Efficient Catalyst for Resorcinol tert-Butylation and n-Heptane Hydroisomerization," J. Mol. Catalysis A: Chemical 221:113-119 (2004).

Ding, et al., "Chemical Trapping Experiments Support a Cation-Radical Mechanism for the Oxidative Polymerization of Aniline," Journal of Polymer Science, Part A: Polymer Chemistry, vol. 37: 2569-2579 (1999).

Dordick, J.S., "Enzymatic Catalysis in Monophasic Organic Dolvents," Enzyme Microb. Technol., 11(4):194-211 (1989).

Dordick, J.S., et al., "Polymerization of Phenols Catalyzed by Peroxidase in Nonaqueous Media," Biotechnology and Bioengineering, 30(1):31-36 (1987).

English Abstract of Kovalev, G. I., et al., "Study of the Effectiveness of Inhibitors in Oxidation of Jet Fuel in a Closed Volume," Deposited Doc., VINITI: 443-82 (1981).

English Abstract of Kovalev, G.I., et al., "Effectiveness of Inhibitors in the Oxidation of Jet Fuel With an Initiator," J. Neftekhimiya (Petroleum Chemistry), 21(2): 287-298 (1981).

Faber, K., "Biotransformations in Organic Chemistry," A Textbook, Fourth Completely Revised and Extended Edition, Springer-Verlag pp: 347-349 (1953).

FS&T 821 "Antioxidant," [online], [retrieved on Oct. 29, 2002]. Retrieved from the Internet <URL: http://class.fst.ohio-state.edu/fst821/>.

FS&T 821 "Food Lipids," [online], Oct. 2001 [retrieved on Oct. 29, 2002]. Retrieved from the Internet <URL: http://classfst.ohio-state.edu/fst821/>.

FST 821 "Course Schedule," [online], [retrieved on Oct. 29, 2002]. Retrieved from the Internet <URL: http://class.fst.ohio-state.edu/fst821/>.

Hatayama, K., et al., "Anti-ulcer Effect of Isoprenyl Flavonoids. III.[1)] Synthesis and Anti-ulcer Activity of Metabolites of 2'-Carboxymethoxly-4,4'-bis(3-methyl-2-butenyloxy)chalcone[2)]," Chemical & Pharmaceutical Bulletin, 33(4), 1327-1333(Apr. 1985).

Heidekum, A., et al., "Nafion/Silica Composite Material Reveals High Catalytic Potential in Acylation Reactions," J. Catal. 188:230-232 (1999).

Hidalgo, M.E., et al., "Antioxidant Activity of Depsides and Depsidones," Phytochemistry, 37(6):1585-1587 (1994).

Hofer, K., et al., "[[(Anilinooxalyl)amino]phenyl] Phosphite Stabilizers for Polypropylene," Chemical Abstracts Service, ZCAPLUS, document No. 77:62780 (1972).

Ikeda, R., et al., "Novel Synthetic Pathway to a Poly(phenylene oxide). Laccase-Catalyzed Oxidative Polymerization of Syringic Acid," Macromolecules, 29:3053-3054 (1996).

International Search Report for related foreign application PCT/US2007/015177, mailed on Jun. 13, 2008.

International Search Report for related foreign application PCT/US2005/044021, mailed on May 22, 2006.

International Search Report for related foreign application PCT/US2005/044022, mailed on May 2, 2006.

International Search Report for related foreign application PCT/US2005/044023, mailed on Nov. 3, 2006.

International Search Report for related foreign application PCT/US2005/044019, mailed on Apr. 28, 2006.

International Search Report for related foreign application PCT/US2005/025646, mailed on Mar. 13, 2006.

International Search Report for related foreign application PCT/US2005/025513, mailed on Mar. 13, 2006.

International Search Report for related foreign application PCT/US2006/006355, mailed on Jul. 31, 2006.

International Search Report for related foreign application PCT/US2006/010985, mailed on Dec. 19. 2006.

International Search Report for related foreign application PCT/US2006/042240, mailed on May 3, 2007.

International Search Report for related foreign application PCT/US2006/042235, mailed on Apr. 27, 2007.

International Search Report for related foreign application PCT/US2006/045929, mailed on Apr. 20, 2007.

Ismail, M.N. and Wazzan, A.A., "Evaluation of New Thermal Stabilizers and Antifatigue Agents for Rubber Vulcanizates," Polymer-Plastics Tech. and Eng., 45:751-758 (2006).

Jayaprakasha, G.K., et al., "Antioxidant Activity of Grape Seed (Vitis vinifera) Extracts on Peroxidation Models in Vitro," Food Chemistry, 73:285-290 (2001).

Jialanella, G.and Pilrma, I., "Synthesis of Poly(vinyl alcohol-co-vinyl gallate) by the Chemical Modification of Poly(vinyl alcohol)," Polymer Bulletin 18:385-389 (1987).

Joossens, J., et al., "Diphenyl Phosphonate Inhibitors for the Urokinase-Type Plasminogen Activator: Optimization of the P4 Position," J. Med. Chem., 49:5785-5793 (2006).

Kamitori, Y., et al., "Silica Gel as an Effective Catalyst for the Alkylation of Phenols and Some Heterocylic Aromatic Compounds," J. Org. Chem. 49: 4161-4165 (1984).

Kazandjian, R.Z., et al., "Enzymatic Analyses in Organic Solvents," Biotechnology and Bioengineering, XXVIII:417-421 (1986).

Khan, K.M., et al., "An Expedient Esterification of Aromatic Carboxylic Acids Using Sodium Bromate and Sodium Hydrogen Sulfite," *Tetrahedron* 59(29):5549-5554 (2003).

Kim, T. H., et al., "Melt Free-Radical Grafting of Hindered Phenol Antioxidant onto Polyethylene," *J. Applied Polymer Science*, 77:2968-2973 (2000).

Klibanov, A.M., et al., "Enzymatic Removal of Toxic Phenols and Anilines from Waste Waters," *J. of Applied Biochemistry*, 2(5):414-421 (1980).

Koshchii, V.A., et al. "Alkylation of Phenol by Alcohols in the Presence of Alumium Phenolate," *Org. Chem.* 24(7):1358-1361 (1988).

Lalancette, J.M., et al. "Metals Intercalated in Graphite. II. The Friedel-Crafts Reactions with $ALCL_3$-Graphite," *Can. J. Chem.* 52:589-591 (1974).

Li, et al., "Novel Multifunctional Polymers from Aromatic Diamines by Oxidative Polymerizations," Chemical Reviews, vol. 102(9): pp. 2925-2943 (2002).

Maki, M., et al., "Weather-Resistant Colored Polypropylene," Chemical Abstracts Service, ZCAPLUS, document No. 89:111364 (1978).

March, J., Advanced Organic Chemistry, McGraw Hill Book Company, New York, pp. 251-259 (1977).

Masada, H. and Oishi, Y., "A New Synthesis of aryl *t*-butyl Ethers," *Chem. Letters*, 57-58 (1978).

Masada, H. et al., "A New Heterogeneous Williamson Synthesis of Ethers Using *t*-alkyl Substrates," The *Chemical Society of Japan* 3:275-282 (1996).

Masada, H., et al., "A New Method for the Williamson Ether Synthesis Using *t*-alkyl Halides in Nonpolar Solvents," The *Chemical Society of Japan*, 2:164-166 (1995).

Mehdipour-Ataei, S., et al., "Novel Diols Containing Ester and Amide Groups and Resulting Poly(ester amide ester)s," *J. Applied Polymer Sci.*, 93:2699-2703 (2004), XP002420014.

Mejias, L., et al. "New Polymers From Natural Phenols Using Horseradish or Soybean Peroxidase," *Macromol. Biosci.*, 2:24-32 (2002).

Ol'dekop, Yu. A., et al. "Simple Synthesis of the tert-butyl Ether of Phenol" Inst. Fiz-Org. Khim., Minsk, USSR. *Zhurnal Obshchei Khimii*, 50(2):475-6 (1980).

Overgaag, M., et al., "Rearrangement of Alkyl Phenyl Ethers Over Dealuminated HY Zeolites Under Liquid-Phase Conditions," *Applied Catalysis A: General, Elsevier Sci.*, 175(1-2):139-146 (1998).

Pätoprstý, V., et al., "$^{13}C$ NMR Study of 3,9-Di(alkylphenoxy)-2,4,8,10-tetraoxa-3,9- diphosphaspiro[5.5]undecanes," *Magnetic Resonance in Chem*, 23(2):122-126 (1985).

Pirozhenko, V.V., et al., "NMR Study of Topomerization of N-Aroyl-p-Benzoquinonemonoimines," *Russian J. of Organic Chem.*, 31(11):1514-1519 (1995).

Quaschning, V., et al., "Properties of Modified Zirconia Used as Friedel-Crafts-Acylation Catalysts," *J. Catal.* 177:164-174 (1998).

Ryu, K., et al., "Peroxidase-Catalyzed Polymerization of Phenols," Biocatalysis in Agricultural Biotechnology, Chapter10:141-157 (1988).

Sakthivel, A., et al., "Vapour Phase Tertiary Butylation of Phenol Over Sulfated Zirconia Catalyst," *Catal. Lett.*, 72(3-4):225-228 (2001).

Sartori G., et al., "Highly Selective Mono-*tert*-butylation of Aromatic Compounds," *Chem. Ind.*, (London), (22):762-763 (1985).

Scharpe, S.L., et al., "Serine Peptidase Modulators, Their Preparation, and Their Therapeutic Use," Chemical Abstracts Service, ZCAPLUS, document No. 131:223514 (1999).

Search Report in international application PCT/US2006/042251 (Feb. 2007).

Singh, A. and Kaplan, D. L., "Biocatalytic Route to Ascorbic Acid-Modified Polymers for Free-Radical Scavenging," *Adv. Matter.*, 15(15):1291-1294 (2003).

Spano, R., et al., "Substituted Anilides of 3-Monoethyl Ester of 4 Hydroxyisophthalic Acid," *J. of Med. Chem.*, 15(5):552-553 (1972).

Thompson, C. Ray, Stability of Carotene in Alfalfa Meal: Effect of Antioxidants, *Industrial & Engineering Chemistry*, 24(5): 922-925 (1950).

XP-002419239, "Discover Our World of Effects for Polyolefins," *Ciba Speciality Chemicals*, (2003).

Tsvetkov, O.N., et al., "Alkylation of Phenols with Higher Olefins. Part I," *Int. Chem. Eng.* 7(1):104-121 (1967).

* cited by examiner

ANTIOXIDANTS AND METHODS OF MAKING AND USING THE SAME

RELATED APPLICATION(S)

This application claims the benefit of U.S. Provisional Application No. 60/853,275, filed on Oct. 20, 2006. The entire teachings of the above application are incorporated herein by reference.

BACKGROUND OF THE INVENTION

Antioxidants are employed to prevent oxidation in a wide range of materials, for example, plastics, elastomers, lubricants, petroleum based products (lubricants, gasoline, aviation fuels, and engine oils), cooking oil, cosmetics, processed food products, and the like. While many antioxidants exist, there is a continuing need for new antioxidants that have improved properties.

SUMMARY OF THE INVENTION

The present invention relates to antioxidant that in general have improved antioxidant properties.

In one embodiment the present invention is directed to compounds represented by Structural Formula I:

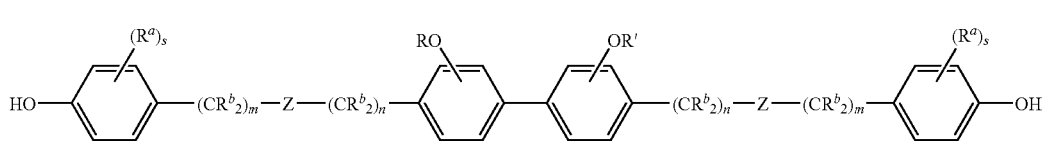

wherein:

R and R' are independently H or optionally substituted alkyl and at least one of R and R' is H;

Z is —C(O)NR$^c$—, —NR$^c$C(O)—, —NR$^c$—, —CR$^c$═N—, —C(O)—, —C(O)O—, —OC(O)—, —O—, —S—, —C(O)OC(O)— or a bond;

R$^c$ is independently H or optionally substituted alkyl;

R$^a$, for each occurrence, is independently an optionally substituted alkyl, optionally substituted aryl, optionally substituted alkoxycarbonyl, optionally substituted ester, —OH, —NH$_2$, —SH;

R$^b$, for each occurrence, is independently H or optionally substituted alkyl;

s, for each occurrence, is independently an integer from 0 to 4; and m and n, for each occurrence, are independently integers from 0 to 6.

In another embodiment, the present invention is directed to a compound represented by Structural Formula II:

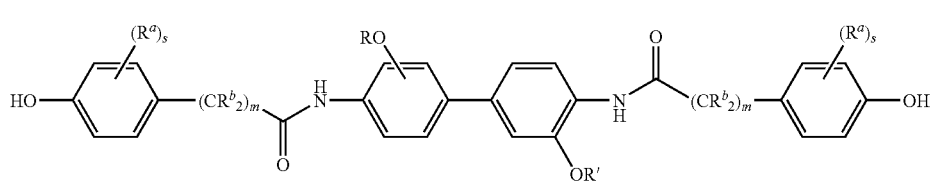

wherein:

R and R' are independently H or optionally substituted alkyl and at least one of R and R' is H;

R$^a$, for each occurrence, is independently an optionally substituted alkyl, optionally substituted aryl, optionally substituted alkoxycarbonyl, optionally substituted ester, —OH, —NH$_2$, or —SH;

R$^b$, for each occurrence, is independently H or optionally substituted alkyl.

s, for each occurrence, is independently an integer from 0 to 4; and m, for each occurrence, is independently an integer from 0 to 6.

In another embodiment, the present invention is directed a compound represented by Structural Formula III:

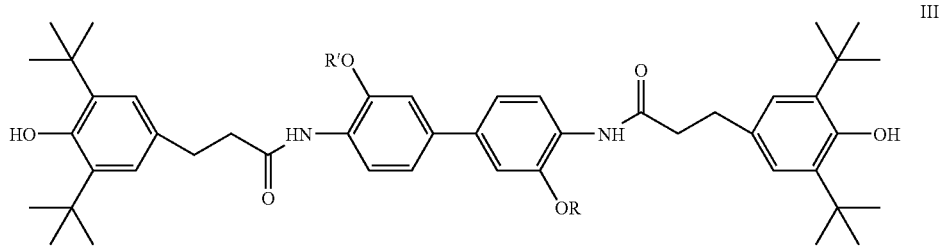

wherein R and R' are independently H or optionally substituted alkyl and at least one of R and R' is H.

In another embodiment the present invention is directed to methods of inhibiting oxidation in an oxidizable material comprising combining the oxidizable material with a compound represented Structural Formula I, II or III.

In certain embodiments, the compounds of the present invention can have enhanced antioxidant activity and better thermal stability compared to commercially available antioxidants.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
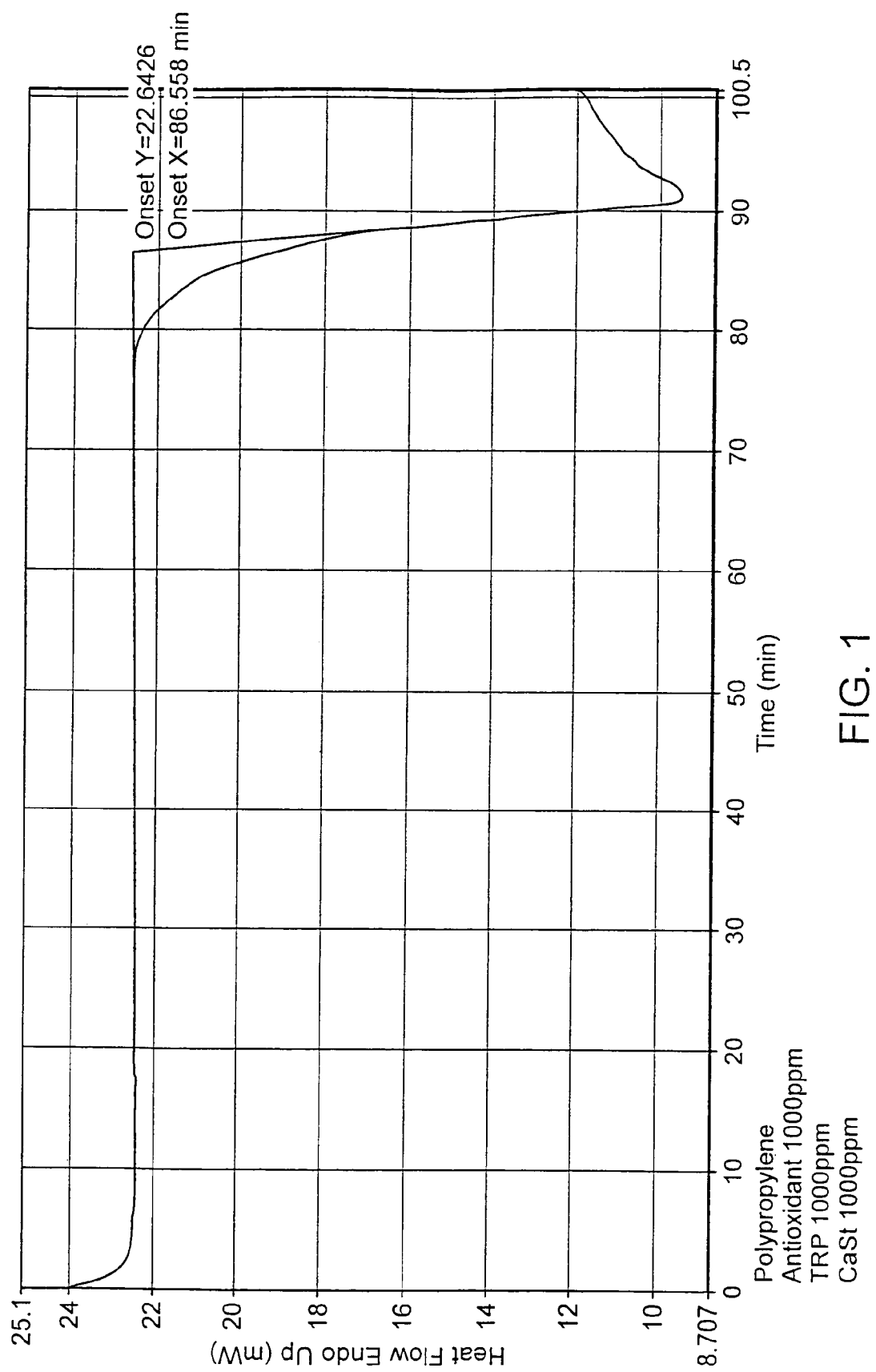
FIG. 1 is a graph showing oxidation induction time of compound A measured according to ASTM procedure.

In certain embodiments the compounds of the present invention comprise sterically hindered groups such as phenol groups. Sterically hindered, as used herein means that the substituent group (e.g., bulky alkyl group) on a ring carbon atom adjacent (or alternatively para) to a ring carbon atom substituted with a phenolic hydroxy group (or thiol or amine group), is large enough to sterically hinder the phenolic hydroxy group (or thiol or amine groups). This steric hindrance, in certain embodiments results in more labile or weak bonding between the oxygen and the hydrogen (or sulfur or nitrogen and hydrogen) and in turn enhances the stability and antioxidant activity (proton donating activity) of the sterically hindered antioxidant.

The antioxidants of the invention include substituted benzene molecules. Some of these benzene molecules are typically based on phenol or a phenol derivative, such that they have at least one hydroxyl or ether functional group. In certain embodiments, the benzene molecules have a hydroxyl group. The hydroxyl group can be a free hydroxyl group and can be protected or have a cleavable group attached to it (e.g., an ester group). Such cleavable groups can be released under certain conditions (e.g., changes in pH), with a desired shelf life or with a time-controlled release (e.g., measured by the half-life), which allows one to control where and/or when an antioxidant can exert its antioxidant effect. The antioxidants can also include analogous thiophenol and aniline derivatives, e.g., where the phenol —OH can be replaced by —SH, —NH—, and the like.

Substituted benzene in an antioxidant of the present invention are also typically substituted with a bulky alkyl group or an n-alkoxycarbonyl group. In certain embodiments, the benzene group is substituted with a bulky alkyl group. In certain other embodiments, the bulky alkyl group is located ortho or meta to a hydroxyl group on the benzene ring, typically ortho. A "bulky alkyl group" is defined herein as an alkyl group that is branched alpha- or beta- to the benzene ring. In certain other embodiments, the alkyl group is branched alpha to the benzene ring. In certain other embodiments, the alkyl group is branched twice alpha to the benzene ring, such as in a tert-butyl group. Other examples of bulky alkyl groups include isopropyl, 2-butyl, 3-pentyl, 1,1-dimethylpropyl, 1-ethyl-1-methylpropyl and 1,1-diethylpropyl. In certain other embodiments, the bulky alkyl groups are unsubstituted, but they can be substituted with a functional group that does not interfere with the antioxidant activity of the molecule. Straight chained alkoxylcarbonyl groups include methoxycarbonyl, ethoxycarbonyl, n-propoxycarbonyl, n-butoxycarbonyl and n-pentoxycarbonyl. N-propoxycarbonyl is a preferred group. Similar to the bulky alkyl groups, n-alkoxycarbonyl groups are optionally substituted with a functional group that does not interfere with the antioxidant activity of the molecule.

In certain embodiment, the compounds of the present invention are represented by Structural Formula I:

R and R' are independently H or optionally substituted alkyl and at least one of R and R' is H. In certain other embodiment, R and R' are independently H or alkyl and at least one of R and R' is H. In certain other embodiment, R and R' are H. In certain other embodiment, R is H and R' is optionally substituted alkyl. In certain other embodiment, R is H and R' is alkyl. In certain other embodiment, R is H and R' is C1-C10 alkyl. More specifically, R' is C10 alkyl. Even more specifically, R' is —(CH$_2$)$_9$CH$_3$.

Z is —C(O)NR$^c$—, —NR$^c$C(O)—, —NR$^c$—, —CR$^c$=N—, —C(O)—, —C(O)O—, —OC(O)—, —O—, —S—, —C(O)OC(O)— or a bond. In certain other embodiments Z is —C(O)O—, —OC(O)—, —C(O)NH—, —NHC(O)—, —NH—, —O— or —C(O)—. In certain other embodiments, Z is —C(O)NH— or —NHC(O)—. Optionally, Z is not —C(O)O—, —OC(O)—, —O— or —NH—. In various embodiments, the present invention relates to a compound of Structural Formula I and the attendant definitions, wherein Z is —OC(O)—. In another embodiment, Z is —C(O)O—. In another embodiment, Z is —C(O)NH—. In another embodiment, Z is —NHC(O)—. In another embodiment, Z is —NH—. In another embodiment, Z is —CH=N—. In another embodiment, Z is —C(O)—. In another embodiment, Z is —O—. In another embodiment, Z is —C(O)OC(O)—. In another embodiment, Z is a bond.

Each R$^c$ is independently —H or optionally substituted alkyl. In certain other embodiments R$^c$ is —H or an alkyl group. In certain other embodiments R$^c$ is —H or a C1-C10 alkyl group. In certain other embodiments R' is —H.

R$^a$, for each occurrence, is independently an optionally substituted alkyl, optionally substituted aryl, optionally substituted alkoxycarbonyl, optionally substituted ester, —OH, —NH$_2$, or —SH. In certain other embodiments, each R$^a$ is independently an optionally substituted alkyl or optionally substituted alkoxycarbonyl. In certain other embodiment each $R^a$ is independently an alkyl or alkoxycarbonyl. In certain other embodiments each $R^a$ is independently a C1-C$_6$ alkyl or a C1-C$_6$ alkoxycarbonyl. In certain other embodiments each $R^a$ is independently tert-butyl or propoxycarbonyl. In certain other embodiments each $R^a$ is independently an alkyl group. In certain embodiments each $R^a$ is independently a bulky alkyl group. Suitable examples of bulky alkyl groups include butyl, sec-butyl, tert-butyl, 2-propyl, 1,1-dimethylhexyl, and the like. In certain embodiments each $R^a$ is tert-butyl. In certain embodiments at least one $R^a$ adjacent to the —OH group is a bulky alkyl group (e.g., butyl, sec-butyl, tert-butyl, 2-propyl, 1,1-dimethylhexyl, and the like). In certain other embodiments both $R^a$ groups adjacent to —OH are bulky alkyl groups (e.g., butyl, sec-butyl, tert-butyl, 2-propyl, 1,1-dimethylhexyl, and the like). In another embodiment, both $R^a$ groups are tert-butyl. In another embodiment, both $R^a$ groups are tert-butyl adjacent to the OH group.

Each n and m are independently integers from 0 to 6. In certain embodiments each n and m are independently integers from 0 to 2.

In another embodiment, the present invention relates to a compound of Structural Formula I wherein n is 0.

In another embodiment, the present invention relates to a compound of Structural Formula I wherein m is 0-2.

alkyl or a C1-C$_6$ alkoxycarbonyl. In certain other embodiments each $R^a$ is independently tert-butyl or propoxycarbonyl. In certain other embodiments each $R^a$ is independently an alkyl group. In certain embodiments each $R^a$ is independently a bulky alkyl group. Suitable examples of bulky alkyl groups include butyl, sec-butyl, tert-butyl, 2-propyl, 1,1-dimethylhexyl, and the like. In certain embodiments each $R^a$ is tert-butyl. In certain embodiments at least one $R^a$ adjacent to the —OH group is a bulky alkyl group (e.g., butyl, sec-butyl, tert-butyl, 2-propyl, 1,1-dimethylhexyl, and the like). In certain other embodiments both $R^a$ groups adjacent to —OH are bulky alkyl groups (e.g., butyl, sec-butyl, tert-butyl, 2-propyl, 1,1-dimethylhexyl, and the like). In another embodiment, both $R^a$ groups are tert-butyl. In another embodiment, both $R^a$ groups are tert-butyl adjacent to the OH group.

Each m is independently an integer from 0 to 6. In certain embodiments each m is independently an integer from 0 to 2. In certain embodiment m is 2.

In another embodiment, the present invention relates to a compound of Structural Formula II wherein m is 2 and the two $R^a$ groups adjacent to the OH are tert-butyl.

Each s is independently an integer from 0 to 4. In certain embodiments, each s is independently an integer from 0 to 2. In certain embodiments, s is 2.

In a first embodiment the present invention is directed to a compound represented by Structural Formula I:

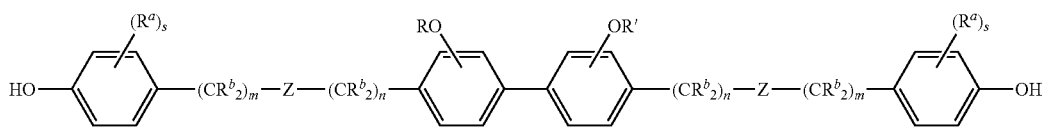

In another embodiment, the present invention relates to a compound of Structural Formula I and the attendant definitions, wherein n is 0 and m is 2.

In another embodiment, the present invention relates to a compound of Structural Formula I wherein n is 0, m is 2, and Z is —NHC(O)— or —C(O)NH—.

In another embodiment, the present invention relates to a compound of Structural Formula I wherein n is 0, m is 2, Z is —NHC(O)—, and the two R groups adjacent to the OH are tert-butyl.

Each s is independently an integer from 0 to 4. In certain embodiments, each s is independently an integer from 0 to 2. In certain embodiments, s is 2.

In certain embodiment, the compounds of the present invention are represented by Structural Formula II:

R and R' are independently H or optionally substituted alkyl and at least one of R and R' is H. In certain other embodiment, R and R' are independently H or alkyl and at least one of R and R' is H. In certain other embodiment, R and R' are H. In certain other embodiment, R is H and R' is optionally substituted alkyl. In certain other embodiment, R is H and R' is alkyl. In certain other embodiment, R is H and R' is C1-C10 alkyl. More specifically, R' is C10 alkyl. Even more specifically, R' is —(CH$_2$)$_9$CH$_3$.

$R^a$, for each occurrence, is independently an optionally substituted alkyl, optionally substituted aryl, optionally substituted alkoxycarbonyl, optionally substituted ester, —OH, —NH$_2$, or —SH. In certain other embodiments, each $R^a$ is independently an optionally substituted alkyl or optionally substituted alkoxycarbonyl. In certain other embodiment each $R^a$ is independently an alkyl or alkoxycarbonyl. In certain other embodiments each $R^a$ is independently a C1-C$_6$ wherein:
R and R' are independently H or optionally substituted alkyl and at least one of R and R' is H;
Z is —C(O)NR$^c$—, —NR$^c$C(O)—, —NR$^c$—, —CR$^c$=N—, —C(O)—, —C(O)O—, —OC(O)—, —O—, —S—, —C(O)OC(O)— or a bond;
$R^c$ is independently H or optionally substituted alkyl;
$R^a$, for each occurrence, is independently an optionally substituted alkyl, optionally substituted aryl, optionally substituted alkoxycarbonyl, optionally substituted ester, —OH, —NH$_2$, —SH;
$R^b$, for each occurrence, is independently H or optionally substituted alkyl;
s, for each occurrence, is independently an integer from 0 to 4; and
m and n, for each occurrence, are independently integers from 0 to 6.

A second embodiment of the present invention is directed to a compound represented by Structural Formula I, wherein:
Z is —C(O)O—, —OC(O)—, —C(O)NH—, —NHC(O)—, —NH—, —O— or —C(O)—;
$R^b$ is H;
$R^a$, for each occurrence is independently an optionally substituted alkyl or optionally substituted alkoxycarbonyl;
n and m, for each occurrence, are independently integers from 0 to 2;
s, for each occurrence, is independently an integer from 0 to 2; and the remainder variables are as described above in the first embodiment.

A third embodiment of the present invention is directed to a compound represented by Structural Formula I, wherein:
Z is —C(O)NH— or —NHC(O)—;

$R^a$, for each occurrence is independently an alkyl or an alkoxycarbonyl;

s is 2; and the remainder of the variables are as described in the second embodiment.

A fourth embodiment of the present invention is directed to a compound represented by Structural Formula I, wherein:

Each $R^a$ is independently an alkyl group, and the remainder of the variables are as described above in the third embodiment. In certain embodiments each $R^a$ is a bulky alkyl group. In certain embodiments two $R^a$ groups are bulky alkyl groups adjacent to the —OH group. In certain embodiments the two R groups are tert-butyl groups adjacent to the —OH group.

A fifth embodiment of the present invention is directed to a compound represented by Structural Formula II, wherein R and R' are independently H or optionally substituted alkyl and at least one of R and R' is H;

$R^a$, for each occurrence, is independently an optionally substituted alkyl, optionally substituted aryl, optionally substituted alkoxycarbonyl, optionally substituted ester, —OH, —NH$_2$, or —SH;

$R^b$, for each occurrence, is independently H or optionally substituted alkyl.

s, for each occurrence, is independently an integer from 0 to 4; and m, for each occurrence, is independently an integer from 0 to 6.

A sixth embodiment of the present invention is directed to a compound Structural Formula II, wherein:

$R^a$, for each occurrence, is independently an optionally substituted alkyl;

$R^b$ is H;

s, for each occurrence, is independently an integer from 0 to 2;

m, for each occurrence, is independently an integer from 0 to 2; and the remainder of the variables are as described above in the fifth embodiment.

A seventh embodiment of the present invention is directed to a compound represented by Structural Formula II, wherein each $R^a$ is independently an alkyl group, and the remainder of the variables are as described above in the sixth embodiment. In certain embodiments each $R^a$ is a bulky alkyl group. In certain embodiments two $R^a$ groups are bulky alkyl groups adjacent to the —OH group. In certain embodiments the two R groups are tert-butyl groups adjacent to the —OH group.

A eighth embodiment of the present invention is directed to a compound represented by Structural Formula III, wherein R and R' are independently H or optionally substituted alkyl and at least one of R and R' is H.

A ninth embodiment of the present invention is directed to a compound represented by Structural Formula III, wherein R is H and R' is an alkyl. More specifically, R' is a C1-C10 alkyl. Even more specifically, R' is a $C_{10}$ alkyl.

A tenth embodiment of the present invention is directed to a compound A represented by the following structural formula:

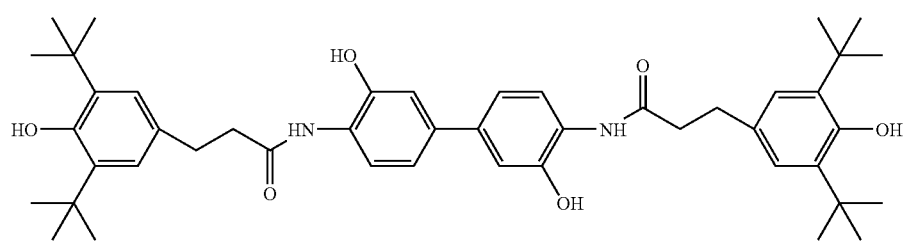

(A)

A eleventh embodiment of the present invention is directed to compound B represented by the following structural formula:

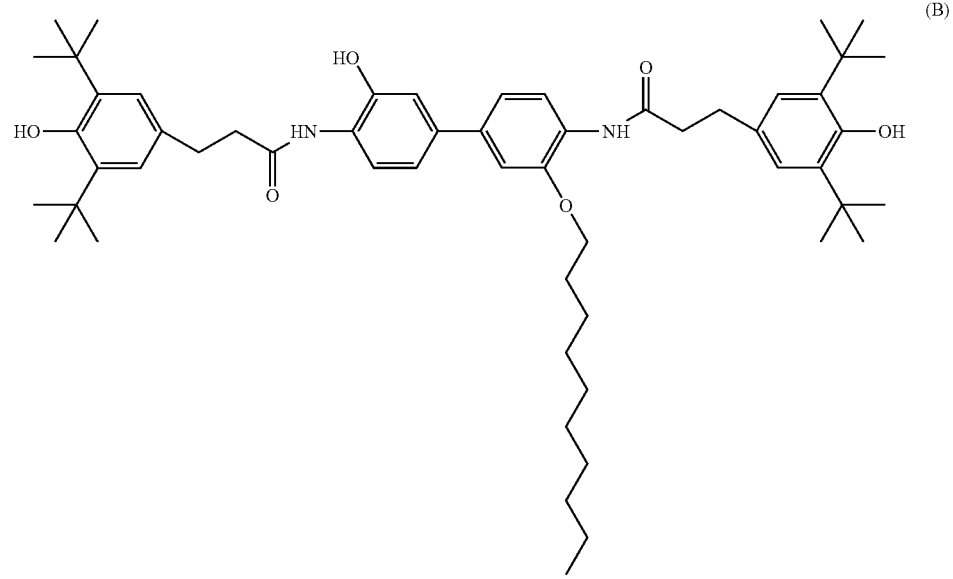

(B)

The term "alkyl" as used herein means a saturated straight-chain, branched or cyclic hydrocarbon. When straight-chained or branched, an alkyl group is typically $C_1$-$C_{20}$, more typically $C_1$-$C_{10}$; when cyclic, an alkyl group is typically $C_3$-$C_{12}$, more typically $C_3$-$C_7$. Examples of alkyl groups include methyl, ethyl, n-propyl, iso-propyl, n-butyl, sec-butyl and tert-butyl and 1,1-dimethylhexyl.

The term "alkoxy" as used herein is represented by —OR, wherein R is an alkyl group as defined above.

The term "carbonyl" as used herein is represented by —C(=O)R, wherein R is an alkyl group as defined above.

The term "alkoxycarbonyl" as used herein is represented by —C(=O)OR, wherein R is an alkyl group as defined above.

The term "aromatic group" includes carbocyclic aromatic rings and heteroaryl rings. The term "aromatic group" may be used interchangeably with the terms "aryl", "aryl ring" "aromatic ring", "aryl group" and "aromatic group".

Carbocyclic aromatic ring groups have only carbon ring atoms (typically six to fourteen) and include monocyclic aromatic rings such as phenyl and fused polycyclic aromatic ring systems in which a carbocyclic aromatic ring is fused to one or more aromatic rings (carbocyclic aromatic or heteroaromatic). Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl.

The term "heteroaryl", "heteroaromatic", "heteroaryl ring", "heteroaryl group" and "heteroaromatic group", used alone or as part of a larger moiety as in "heteroaralkyl" refers to heteroaromatic ring groups having five to fourteen members, including monocyclic heteroaromatic rings and polycyclic aromatic rings in which a monocyclic aromatic ring is fused to one or more other aromatic ring (carbocyclic or heterocyclic). Heteroaryl groups have one or more ring heteroatoms. Examples of heteroaryl groups include 2-furanyl, 3-furanyl, N-imidazolyl, 2-imidazolyl, 4-imidazolyl, 5-imidazolyl, 3-isoxazolyl, 4-isoxazolyl, 5-isoxazolyl, oxadiazolyl, oxadiazolyl, 2-oxazolyl, 4-oxazolyl, 5-oxazolyl, N-pyrazolyl, 3-pyrazolyl, 4-pyrazolyl, 5-pyrazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-thiazolyl, 4-thiazolyl, 5-thiazolyl, triazolyl, tetrazolyl, 2-thienyl, 3-thienyl, carbazolyl, benzothienyl, benzofuranyl, indolyl, quinolinyl, benzothiazole, benzooxazole, benzimidazolyl, isoquinolinyl and isoindolyl. Also included within the scope of the term "heteroaryl", as it is used herein, is a group in which an aromatic ring is fused to one or more non-aromatic rings (carbocyclic or heterocyclic).

An "arylene" group as defined herein is a bivalent group represented by —Ar—, wherein Ar is an aromatic group as defined above.

The term non-aromatic heterocyclic group used alone or as part of a larger moiety refers to non-aromatic heterocyclic ring groups having three to fourteen members, including monocyclic heterocyclic rings and polycyclic rings in which a monocyclic ring is fused to one or more other non-aromatic carbocyclic or heterocyclic ring or aromatic ring (carbocyclic or heterocyclic). Heterocyclic groups have one or more ring heteroatoms, and can be saturated or contain one or more units of unsaturation. Examples of heterocyclic groups include piperidinyl, piperizinyl, pyrrolidinyl, pyrazolidinyl, imidazolidinyl, tetrahydroquinolinyl, inodolinyl, isoindolinyl, tetrahydrofuranyl, oxazolidinyl, thiazolidinyl, dioxolanyl, dithiolanyl, tetrahydropyranyl, dihydropyranyl, azepanyl and azetidinyl The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heteroaryl or non-aromatic heterocyclic group. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR' (as in N-substituted pyrrolidinyl), wherein R' is a suitable substituent for the nitrogen atom in the ring of a non-aromatic nitrogen-containing heterocyclic group, as defined below. Preferably the nitrogen is unsubstituted.

As used herein the term non-aromatic carbocyclic ring as used alone or as part of a larger moiety refers to a non-aromatic carbon containing ring which can be saturated or contain one or more units of unsaturation, having three to fourteen atoms including monocyclic and polycyclic rings in which the carbocyclic ring can be fused to one or more non-aromatic carbocyclic or heterocyclic rings or one or more aromatic (carbocyclic or heterocyclic) rings An optionally substituted aryl group as defined herein may contain one or more substitutable ring atoms, such as carbon or nitrogen ring atoms. Examples of suitable substituents on a substitutable ring carbon atom of an aryl group include halogen (e.g., —Br, Cl, I and F), —OH, C1-C4 alkyl, C1-C4 haloalkyl, —NO₂, C1-C4 alkoxy, C1-C4 haloalkoxy, —CN, —NH₂, C1-C4 alkylamino, C1-C4 dialkylamino, —C(O)NH₂, —C(O)NH(C1-C4 alkyl), —C(O)(C1-C4 alkyl), —OC(O)(C1-C4 alkyl), —OC(O)(aryl), —OC(O)(substituted aryl), —OC(O)(aralkyl), —OC(O)(substituted aralkyl), —NHC(O)H, —NHC(O)(C1-C4 alkyl), —C(O)N(C1-C4 alkyl)₂, —NHC(O)O—(C1-C4 alkyl), —C(O)OH, —C(O)O—(C1-C4 alkyl), —NHC(O)NH₂, —NHC(O)NH(C1-C4 alkyl), —NHC(O)N(C1-C4 alkyl)₂, —NH—C(=NH)NH₂, —SO₂NH₂—SO₂NH(C1-C3alkyl), —SO₂N(C1-C3alkyl)₂, NHSO₂H, NHSO₂(C1-C4 alkyl) and aryl. Preferred substituents on aryl groups are as defined throughout the specification. In certain embodiments aryl groups are unsubstituted.

Examples of suitable substituents on a substitutable ring nitrogen atom of an aryl group include C1-C4 alkyl, NH₂, C1-C4 alkylamino, C1-C4 dialkylamino, —C(O)NH₂, —C(O)NH(C1-C4 alkyl), —C(O)(C1-C4 alkyl), —CO₂R, —C(O)C(O)R, —C(O)CH₃, —C(O)OH, —C(O)O—(C1-C4 alkyl), —SO₂NH₂—SO₂NH(C1-C3alkyl), —SO₂N(C1-C3alkyl)₂, NHSO₂H, NHSO₂(C1-C4 alkyl), —C(=S)NH₂, —C(=S)NH(C1-C4 alkyl), —C(=S)N(C1-C4 alkyl)₂, —C(=NH)—N(H)₂, —C(=NH)—NH(C1-C4 alkyl) and —C(=NH)—N(C1-C4 alkyl)₂, An optionally substituted alkyl group or non-aromatic carbocyclic or heterocyclic group as defined herein may contain one or more substituents. Examples of suitable substituents for an alkyl group include those listed above for a substitutable carbon of an aryl and the following: =O, =S, =NNHR, =NN(R)₂, =NNHC(O)R, =NNHCO₂(alkyl), =NNHSO₂(alkyl), =NR, spiro cycloalkyl group or fused cycloalkyl group. R** in each occurrence, independently is —H or C1-C6 alkyl. Preferred substituents on alkyl groups are as defined throughout the specification. In certain embodiments optionally substituted alkyl groups are unsubstituted.

A "spiro cycloalkyl" group is a cycloalkyl group which shares one ring carbon atom with a carbon atom in an alkylene group or alkyl group, wherein the carbon atom being shared in the alkyl group is not a terminal carbon atom.

In yet another embodiment, the present invention is a method of producing a compound herein using methods known in the art of organic and polymer chemistry.

In certain embodiments, this invention can allow synthesizing the antioxidants described herein cost effectively.

In various embodiments, the antioxidants of the present invention can be prepared by the modification of compounds represented by the following Structural Formula:

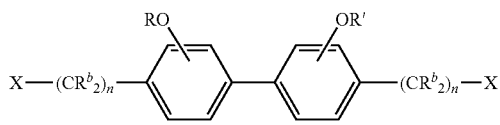

wherein X is —C(O)OH, —OH, —NRC$_2$ or —SH and the remainder of the variables are as described above.

In various embodiments, the antioxidants of the present invention can be prepared by coupling of the compounds represented by the following Structural Formula:

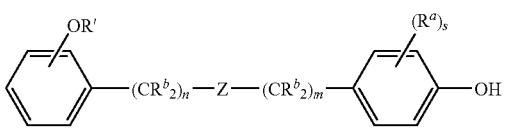

wherein the variables are as described above.

In various embodiments, intermediates in the compounds of the present invention can be prepared by methods described in U.S. Publication Nos.: 2006/0041094 and 2006/0041087 U.S. application Ser. Nos. 11/292,813, 11/293,050, 11/293,049 and 11/293,844, 11/389,564, the entire teachings of each of these references are incorporated herein by reference In certain embodiments the antioxidants of the present invention can have significantly higher antioxidant activities along with improved thermal stability and performance in a wide range of materials including but not limited to plastics, elastomers, lubricants, petroleum based products (lubricants, gasoline, aviation fuels, and engine oils), cooking oil, cosmetics, processed food products, compared to commercially available antioxidants. In general, the antioxidants of the Structural Formulas I, II, and III have superior performance in materials including but not limited to polyolefins.

The compounds of the present invention can be used as antioxidants to inhibit oxidation of an oxidizable material. Such as, for example to increase the shelf life of an oxidizable material.

The antioxidant compounds of the present invention can be employed to inhibit the oxidation of an oxidizable material, for example by contacting the material with an antioxidant compound of the present invention.

For purposes of the present invention, a method of "inhibiting oxidation" is a method that inhibits the propagation of a free radical-mediated process. Free radicals can be generated by heat, light, ionizing radiation, metal ions and some proteins and enzymes. Inhibiting oxidation also includes inhibiting reactions caused by the presence of oxygen, ozone or another compound capable of generating these gases or reactive equivalents of these gases.

As used herein the term "oxidizable material" is any material which is subject to oxidation by free-radicals or oxidative reaction caused by the presence of oxygen, ozone or another compound capable of generating these gases or reactive equivalents thereof.

In certain embodiments, the oxidizable material is an organic polymer or plastic. In certain embodiments, the oxidizable material is an elastomer. In certain embodiments, the oxidizable material is a lubricant. In certain embodiments, the oxidizable material is a petroleum based product. In certain embodiments, the oxidizable material is an edible oil or cooking oil. In certain embodiments, the oxidizable material is a cosmetic. In certain embodiments, the oxidizable material is a processed food product.

In particular the oxidizable material is a lubricant or a mixture of lubricants.

The shelf life of many materials and substances contained within the materials, such as packaging materials, are enhanced by the presence of the antioxidants of the present invention. The addition of an antioxidant of the present invention to a packaging material is believed to provide additional protection to the product contained inside the package. In addition, the properties of many packaging materials themselves, particularly polymers, are enhanced by the presence of an antioxidant regardless of the application (i.e., not limited to use in packaging). Common examples of packaging materials include paper, cardboard and various plastics and polymers. A packaging material can be coated with an antioxidant (e.g., by spraying the antioxidant or by applying as a thin film coating), blended with or mixed with an antioxidant, or otherwise have an antioxidant present within it. In one example, a thermoplastic such as polyethylene, polypropylene or polystyrene can be melted in the presence of an antioxidant in order to minimize its degradation during the polymer processing.

The lifetime of lubricants, lubricant oils, mixtures thereof and compositions comprising lubricants and lubricant oils in general can be improved by contacting the lubricant, lubricant oil, mixtures thereof or composition comprising the lubricant or lubricant oil or mixtures thereof with compounds of the present invention, as described herein.

In certain embodiments of the present invention, polyolefins and mixtures of polyolefins can be stabilized by contacting the polyolefin or mixture of polyolefins with a compound of the present invention. These polyolefins and mixtures of polyolefins, include, but are not limited to substituted polyolefins, polyacrylates, polymethacrylates and copolymers of polyolefins. The following are examples of some types of polyolefins which can be stabilized by the methods of the present invention:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), very low density polyethylene (VLDPE) and ultra low density polyethylene (ULDPE).

Polyolefins, i.e. the polymers of monoolefins exemplified in the preceding paragraph, for example polyethylene and polypropylene, can be prepared by different, and especially by the following, methods:

i) radical polymerization (normally under high pressure and at elevated temperature).

ii) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, Ia and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1., for example, mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Blends of polymers mentioned under 1. with impact modifiers such as ethylene-propylene-diene monomer copolymers (EPDM), copolymers of ethylene with higher alpha-olefins (such as ethylene-octene copolymers), polybutadiene, polyisoprene, styrene-butadiene copolymers, hydrogenated styrene-butadiene copolymers, styrene-isoprene copolymers, hydrogenated styrene-isoprene copolymers. These blends are commonly referred to in the industry as TPO's (thermoplastic polyolefins).

In certain particular embodiments polyolefins of the present invention are for example polypropylene homo- and copolymers and polyethylene homo- and copolymers. For instance, polypropylene, high density polyethylene (HDPE), linear low density polyethylene (LLDPE) and polypropylene random and impact (heterophasic) copolymers.

In certain embodiments of the present invention, 50% to 20% by weight of the antioxidants of the present invention are added to the polyolefin. In certain other embodiments of the present invention, 10% to 5% by weight of the antioxidants of the present invention are added to the polyolefin. In certain other embodiments of the present invention, 0.1% to 2% by weight of the antioxidants of the present invention are added to the polyolefin. In certain other embodiments of the present invention, 0.001% to 0.5% by weight of the antioxidants of the present invention are added to the polyolefin. This percentage varies depending upon their end application and type of the polyolefin.

In certain embodiments of the present invention the antioxidants of the present invention are usually added to the polyolefin with stirring at between 0 and 100° C., between 10 and 80° C., between 20-30° C. or at room temperature.

In certain embodiments the antioxidants of the present invention can be mixed with other antioxidants or additives to produce formulations, such as those described in Provisional Patent Application No. 60/742,150, filed Dec. 2, 2005, Title: Lubricant Composition, by Kumar, Rajesh, et al., and Provisional Patent Application No. 60/731,325, filed Oct. 27, 2005, Title: Stabilized Polyolefin Composition, by Kumar, Rajesh, et al., the entire contents of each of which are incorporated herein by reference.

EXEMPLIFICATION

Example 1

Preparation of Compound A

In a 1 L 3-necked flask, equipped with a stirrer, and a Dean-Starke water trap carrying a reflux condenser, was charged 21.6 g (0.1 mole) of 3,3'-dihydroxybenzidine, 55.6 g (0.2 mole) of 3,5-di-tert-butyl-4-hydroxyphenylpropionic acid, 1.22 g (0.02 mole) of powdered boric acid, 500 ml of toluene and 50 ml of dimethyl sulfoxide. Reactants were heated at 140° C. for 48 h with removal of water. At the end of the reaction, toluene was distilled off under reduced pressure and the residual melt was added to 1 lit. of water and stirred for 6 h. Solids were separated by filtration. Crude solids obtained were dissolved in 500 ml acetone and to this solution was added 10 ml conc. hydrochloric acid. This acidified solution was slowly dropped with stirring in 2 lit. of water and the solids separated out collected by filtration and washed with water until the filtrate showed neutral pH. These solids were further purified by dissolving in 500 ml of methanol and treating with 3.5 g of activated charcoal at ambient temperature for 30 min. The solution was filtered and the filtrate was then added to 1 lit. of aqueous 10% sodium bicarbonate solution with vigorous stirring. Solids were collected by vacuum filtration and washed with water until the filtrate showed neutral pH. The solids were dried in vacuum at 50° C. There was obtained 63 g (85.5%) of (I) as off white powder.

Example 2

Improved Oxidation Induction Times of the Antioxidants Compound A

Compound A was evaluated and found to have desirable antioxidant properties. The antioxidant properties of this novel compound were studied by mixing 1000 ppm of compound A in polypropylene with triphosphite secondary antioxidant (1000 ppm) and CaStereate as acid scavenger. The oxidation induction time (OIT) was determined using ASTM D3895 method by differential scanning calorimetry (DSC). As shown in FIG. 1, compound A has an oxidation induction time of 85 min.

The entire contents of each of the following are incorporated herein by reference.

Provisional Patent Application No. 60/632,893, filed Dec. 3, 2004, Title: Process For The Synthesis Of Polyalkylphenol Antioxidants, by Suizhou Yang, et al;

Patent application Ser. No. 11/292,813 filed Dec. 2, 2005, Title: Process For The Synthesis Of Polyalkylphenol Antioxidants, by Suizhou Yang, et al;

Provisional Patent Application No. 60/633,197, filed Dec. 3, 2004, Title: Synthesis Of Sterically Hindered Phenol Based Macromolecular Antioxidants, by Ashish Dhawan, et al.;

Patent application Ser. No. 11/293,050; filed Dec. 2, 2005, Title: Synthesis Of Sterically Hindered Phenol Based Macromolecular Antioxidants, by Ashish Dhawan, et al.;

Provisional Patent Application No. 60/633,252, filed Dec. 3, 2004, Title: One Pot Process For Making Polymeric Antioxidants, by Vijayendra Kumar, et al.;

Patent application Ser. No. 11/293,049; filed Dec. 2, 2005, Title: One Pot Process For Making Polymeric Antioxidants, by Vijayendra Kumar, et al.;

Provisional Patent Application No. 60/633,196, filed Dec. 3, 2004, Title: Synthesis Of Aniline And Phenol-Based Macromonomers And Corresponding Polymers, by Rajesh Kumar, et al.;

Patent application Ser. No. 11/293,844; filed Dec. 2, 2005, Title: Synthesis Of Aniline And Phenol-Based Macromonomers And Corresponding Polymers, by Rajesh Kumar, et al.;

Patent application Ser. No. 11/184,724, filed Jul. 19, 2005, Title: Anti-Oxidant Macromonomers And Polymers And Methods Of Making And Using The Same, by Ashok L. Cholli;

Patent application Ser. No. 11/184,716, filed Jul. 19, 2005, Title: Anti-Oxidant Macromonomers And Polymers And Methods Of Making And Using The Same, by Ashok L. Cholli;

Patent application Ser. No. 11/360,020, filed Feb. 22, 2006, Title: Nitrogen And Hindered Phenol Containing Dual Functional Macromolecules: Synthesis And Their Antioxidant Performances In Organic Materials, by Rajesh Kumar, et al.

Provisional Patent Application No. 60/655,169, filed Mar. 25, 2005, Title: Alkylated Macromolecular Antioxidants And Methods Of Making, And Using The Same, by Rajesh Kumar, et al.

Provisional Patent Application No. 60/731,125, filed Oct. 27, 2005, Title: Macromolecular Antioxidants And Polymeric Macromolecular Antioxidants, by Ashok L. Cholli, et al.

Provisional Patent Application No. 60/731,021, filed Oct. 27, 2005, Title: Macromolecular Antioxidants Based On Sterically Hindered Phenols And Phosphites, by Ashok L. Cholli, et al.

Provisional Patent Application No. 60/742,150, filed Dec. 2, 2005, Title: Lubricant Composition, by Kumar, Rajesh, et al.

Provisional Patent Application No. 60/731,325, filed Oct. 27, 2005, Title: Stabilized Polyolefin Composition, by Kumar, Rajesh, et al.

Patent application Ser. No. 11/040,193, filed Jan. 21, 2005, Title: Post-Coupling Synthetic Approach For Polymeric Antioxidants, by Ashok L. Choll, et al.;

Patent Application No. PCT/US2005/001948, filed Jan. 21, 2005, Title: Post-Coupling Synthetic Approach For Polymeric Antioxidants, by Ashok L. Cholli et al.;

Patent Application No. PCT/US2005/001946, filed Jan. 21, 2005, Title: Polymeric Antioxidants, by Ashok L. Choll, et al.;

Patent Application No. PCT/US03/10782, filed Apr. 4, 2003, Title: Polymeric Antioxidants, by Ashok L. Choll, et al.;

Patent application Ser. No. 10/761,933, filed Jan. 21, 2004, Title: Polymeric Antioxidants, by Ashish Dhawan, et al.;

Patent application Ser. No. 10/408,679, filed Apr. 4, 2003, Title: Polymeric Antioxidants, by Ashok L. Choll, et al.;

U.S. Pat. No. 6,770,785 B1

U.S. Pat. No. 5,834,544

Neftekhimiya (1981), 21(2): 287-298.

While this invention has been particularly shown and described with references to preferred embodiments thereof, it will be understood by those skilled in the art that various changes in form and details may be made therein without departing from the scope of the invention.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. A compound represented by Structural Formula I:

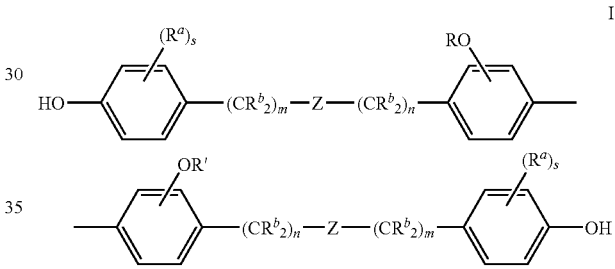

wherein:
R and R' are independently H or optionally substituted alkyl and at least one of R and R' is H;

Z is —C(O)NR$^c$—, —NR$^c$C(O)—, —NR$^c$—, —CR$^c$=N—, —C(O)—, —C(O)O—, —OC(O)—, —O—, —S—, —C(O)OC(O)— or a bond;

R$^c$ is independently H or optionally substituted alkyl;

R$^a$, for each occurrence, is independently an optionally substituted alkyl, optionally substituted aryl, optionally substituted alkoxycarbonyl, optionally substituted ester, —OH, —NH$_2$, —SH;

R$^b$, for each occurrence, is independently H or optionally substituted alkyl;

s, for each occurrence, is independently integers from 0 to 4; and m and n, for each occurrence, are independently integers from 0 to 6.

2. The compound of claim 1, wherein:

Z is —C(O)O—, —OC(O)—, —C(O)NH—, —NHC(O)—, —NH—, —O— or —C(O)—;

R$^b$ is H;

R$^a$, for each occurrence is independently an optionally substituted alkyl or optionally substituted alkoxycarbonyl;

n and m, for each occurrence, are independently integers from 0 to 2; and s, for each occurrence, is independently an integer from 0 to 2.

3. The compound of claim 2, wherein:
Z is —C(O)NH— or —NHC(O)—;
R$^a$, for each occurrence is independently an alkyl or an alkoxycarbonyl;
and s is 2.

4. The compound of claim 3, wherein each R$^a$ is independently an alkyl group.

5. The compound of claim 1, wherein the compound is represented by Structural Formula II:

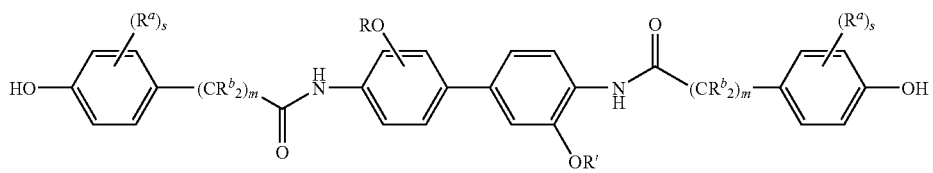

wherein:
R and R' are independently H or optionally substituted alkyl and at least one of R and R' is H;
R$^a$, for each occurrence, is independently an optionally substituted alkyl, optionally substituted aryl, optionally substituted alkoxycarbonyl, optionally substituted ester, —OH, —NH$_2$, or —SH;
R$^b$, for each occurrence, is independently H or optionally substituted alkyl.
s, for each occurrence, is independently an integer from 0 to 4; and
m, for each occurrence, is independently an integer from 0 to 6.

6. The compound of claim 5, wherein:
R$^a$, for each occurrence, is independently an optionally substituted alkyl;
R$^b$ is H;
s, for each occurrence, is independently an integer from 0 to 2; and
m, for each occurrence, is independently an integer from 0 to 2.

7. The compound of claim 6, wherein R$^a$ is independently an alkyl and s is 2.

8. The compound of claim 1, wherein the compound is represented by Structural Formula III:

wherein:
R and R' are independently H or optionally substituted alkyl and at least one of R and R' is H.

9. The compound of claim 8, wherein R and R' are H.

10. The compound of claim 8, wherein R is H and R' is an alkyl.

11. The compound of claim 10, wherein R' is a $C_1$-$C_{15}$ alkyl.

12. The compound of claim 11, wherein R' is a $C_{10}$ alkyl.

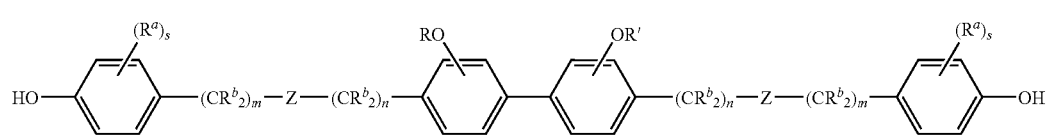

13. The compound of claim 12, wherein R'=—(CH$_2$)$_9$CH$_3$.

14. A method of inhibiting oxidation in an oxidizable material comprising combining the oxidizable material with a compound represented by Structural Formula I wherein:
R and R' are independently H or optionally substituted alkyl and at least one of R and R' is H;
Z is —C(O)NR$^c$—, —NR$^c$C(O)—, —NR$^c$—, —CR$^c$=N—, —C(O)—, —C(O)O—, —OC(O)—, —O—, —S—, —C(O)OC(O)— or a bond;
R$^c$ is independently H or optionally substituted alkyl;
R$^a$, for each occurrence, is independently an optionally substituted alkyl, optionally substituted aryl, optionally substituted alkoxycarbonyl, optionally substituted ester, —OH, —NH$_2$, —SH;
R$^b$, for each occurrence, is independently H or optionally substituted alkyl;
s, for each occurrence, is independently an integer from 0 to 4; and

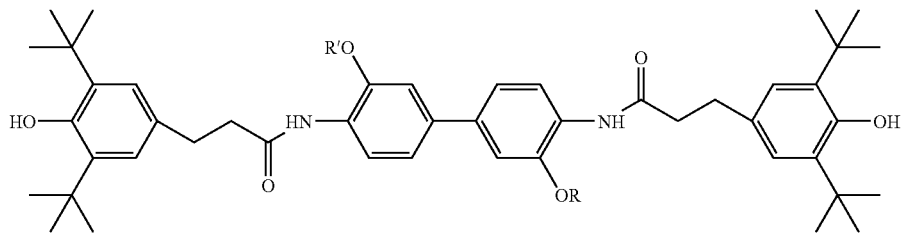

m and n, for each occurrence, are independently integers from 0 to 6.

15. The method of claim 14, wherein
Z is —C(O)O—, —OC(O)—, —C(O)NH—, —NHC(O)—, —NH—, —O— or —C(O)—;
$R^b$ is H;
$R^a$, for each occurrence is independently an optionally substituted alkyl or optionally substituted alkoxycarbonyl;
n and m, for each occurrence, are independently integers from 0 to 2; and
s, for each occurrence, is independently an integer from 0 to 2.

16. The method of claim 15, wherein:
Z is —C(O)NH— or —NHC(O)—;
$R^a$, for each occurrence is independently an alkyl or an alkoxycarbonyl;
and s is 2.

17. The method of claim 16, wherein each $R^a$ is independently an alkyl group.

18. The method of claim 14, wherein the compound is represented by Structural Formula II:

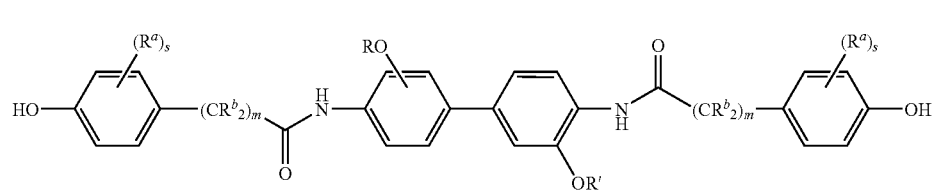

wherein:
R and R' are independently H or optionally substituted alkyl and at least one of R and R' is H;
$R^a$, for each occurrence, is independently an optionally substituted alkyl, optionally substituted aryl, optionally substituted alkoxycarbonyl, optionally substituted ester, —OH, —NH$_2$, or —SH;
$R^b$, for each occurrence, is independently H or optionally substituted alkyl.

s, for each occurrence, is independently an integer from 0 to 4; and m, for each occurrence, is independently an integer from 0 to 6.

19. The method of claim 18, wherein:

$R^a$, for each occurrence, is independently an optionally substituted alkyl;

$R^b$ is H;

s, for each occurrence, is independently an integer from 0 to 2; and m, for each occurrence, is independently an integer from 0 to 2.

20. The method of claim 19, wherein $R^a$ is independently an alkyl and s is 2.

21. The method of claim 14, wherein the compound is represented by Structural Formula III:

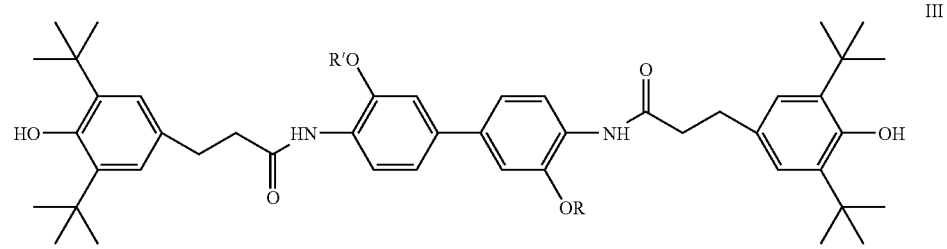

wherein:
R and R' are independently H or optionally substituted alkyl and at least one of R and R' is H.

22. The method of claim 21, wherein R and R' are H.

23. The method of claim 21, wherein R is H and R' is an alkyl.

24. The method of claim 23, wherein R' is a $C_1$-$C_{15}$ alkyl.

25. The method of claim 24, wherein R' is a $C_{10}$ alkyl.

26. The method of claim 25, wherein R'=—$(CH_2)_9CH_3$.

27. The method of claim 14, wherein the oxidizable material is an organic polymer or plastic.

28. The method of claim 14, wherein the oxidizable material is an elastomer.

29. The method of claim 14, wherein the oxidizable material is a lubricant.

30. The method of claim 14, wherein the oxidizable material is a petroleum based product.

31. The method of claim 14, wherein the oxidizable material is an edible oil or cooking oil.

32. The method of claim 14, wherein the oxidizable material is a cosmetic.

33. The method of claim 14, wherein the oxidizable material is a processed food product.

* * * * *

UNITED STATES PATENT AND TRADEMARK OFFICE
CERTIFICATE OF CORRECTION

PATENT NO. : 7,767,853 B2
APPLICATION NO. : 11/975141
DATED : August 3, 2010
INVENTOR(S) : Ashok L. Cholli et al.

It is certified that error appears in the above-identified patent and that said Letters Patent is hereby corrected as shown below:

In the Claims:

Column 17, Claim 5, Line 10 delete

"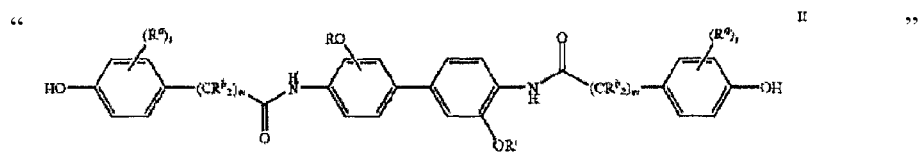"

and insert

--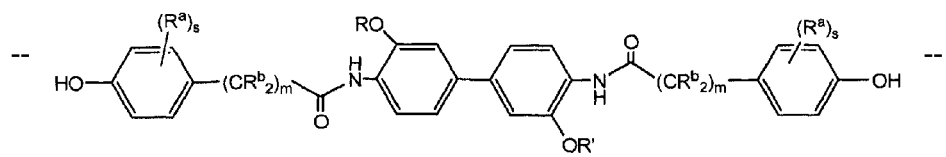--

Column 19, Claim 18, Line 23 delete

"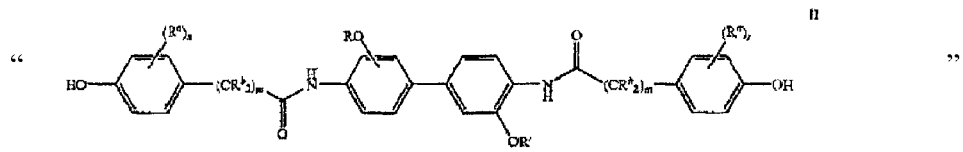"

and insert

--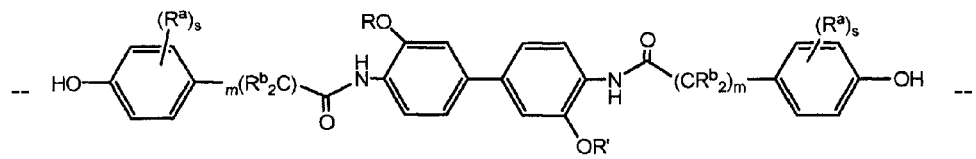--

Signed and Sealed this

Twenty-sixth Day of October, 2010

David J. Kappos
*Director of the United States Patent and Trademark Office*